United States Patent [19]

Meier et al.

[11] Patent Number: 5,246,966

[45] Date of Patent: Sep. 21, 1993

[54] SUBSTITUTED ALKENOIC ACID AND ITS DERIVATIVES

[75] Inventors: Heinrich Meier; John E. B. Ransohoff, both of Wuppertal, Fed. Rep. of Germany; Trevor S. Abram, Bucks, United Kingdom; Peter Norman, Bucks, United Kingdom; Tudhope Stephen R., Windsor Berks, United Kingdom; Phillip J. Gardiner, High Wycombe, United Kingdom; Nigel J. Cuthbert, Great Missenden, United Kingdom; Hilary P. Francis, Woodley, United Kingdom

[73] Assignee: Bayer Aktiengesellschaft, Leverkusen, Fed. Rep. of Germany

[21] Appl. No.: 816,162

[22] Filed: Dec. 30, 1991

[30] Foreign Application Priority Data

Jan. 10, 1991 [GB] United Kingdom ............... 9100493

[51] Int. Cl.⁵ ............... A61K 31/235; A61K 31/19; C07C 321/28; C07C 69/732

[52] U.S. Cl. ............... 514/533; 514/568; 560/9; 560/17; 560/55; 560/60; 562/431; 562/432; 562/470

[58] Field of Search ............... 560/9, 17, 55, 60; 562/431, 432, 470; 514/533, 568

[56] References Cited

FOREIGN PATENT DOCUMENTS 0235452  9/1987  European Pat. Off. .
0341551  11/1989  European Pat. Off. .

Primary Examiner—José G. Dees
Assistant Examiner—Vera C. Clarke
Attorney, Agent, or Firm—Sprung Horn Kramer & Woods

[57] ABSTRACT

The new substituted alkenoic acid derivatives can be prepared by reacting the appropriate aldehyde with a phosphonium compound. The compounds have leukotriene antagonistic properties and can be incorporated into pharmaceutical compositions.

9 Claims, No Drawings

SUBSTITUTED ALKENOIC ACID AND ITS DERIVATIVES

The invention relates to a substituted alkenoic acid and its derivatives, a process for the preparation and their use in medicaments.

The GB 2 184 121 describes phenethyl sulfides with leukotriene antagonistic properties. The more active compounds of GB 2 184 121 are insufficiently stable for pharmaceutical use.

The GB 2 218 416 describes phenoxy alkoxy substituted alkenoic acid derivatives which are leukotriene antagonists and accordingly indicated for the therapeutic use in the treatment of diseases in which leukotrienes are implicated.

The present invention relates to a new substituted alkenoic acid derivative of the general formula

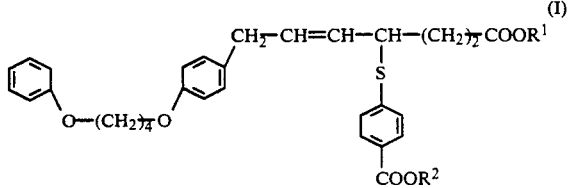

wherein $R^1$, $R^2$ are identical or different and denote hydrogen, branched or straight chain $C_1$-$C_6$-alkyl or benzyl, where appropriate in an isomeric form and their salts.

Surprisingly, the substances according to the invention are potent leukotriene antagonists and have a superior activity compared with compounds known in the prior art.

The compounds according to the invention when bearing an acidic function ($R^1$, $R^2$=H) can also exist in form of their salts. In general, the salts which may be mentioned in this context are those with organic or inorganic bases.

Physiologically acceptable salts are preferred within the scope of the present invention. Examples of such salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases for example useful in the preparation of such salts include ammonium, sodium or potassium hydroxide, sodium or potassium carbonate and bicarbonate, calcium hydroxide, methylamine, diethylamine, ethylene diamine, triethylamine, cyclohexylamine and ethanolamine.

Particularly preferred are the potassium and sodium salts of the compounds according to the invention. But it is to be understood that other, non-pharmaceutical salts are included in the invention since they may be useful for identification, characterization or purification of the compounds.

As the compounds according to the invention contain a double bond, they can exist in two stereoisomeric forms which can have the E configuration or the Z configuration on the double bond.

Moreover, the compounds of the invention possess an asymmetric carbon atom at the main chain carbon atom to which the sulfur side chain is attached and this results in R and S isomers or racemic mixtures thereof. The invention relates both to the individual isomers and to the mixtures thereof.

Isomers can be isolated from racemic mixtures by conventional methods such as described by E. L. Eliel, Stereochemistry of carbon compounds, McGraw Hill, 1962, for example by the preparation of diastereomers with subsequent liberation of the enantiomers.

Furthermore enantiomerically pure end products can be prepared from enantiomerically pure starting material. Alternatively they may be prepared by reaction of an achiral intermediate with a chiral reagent which gives a chiral product of high optical purity.

Preferred compounds of the general formula (I) are those where $R^1$, $R^2$ are identical or different and denote hydrogen, or branched or straight-chain $C_1$-$C_4$-alkyl, where appropriate in an isomeric form and their salts.

Particularly preferred compounds of the general formula (I) are those where $R^1$, $R^2$ are identical or different and denote hydrogen, methyl or ethyl, where appropriate in an isomeric form and their salts.

Very particularly preferred are compounds of the general formula (I) wherein $R^1$ and $R^2$ denote hydrogen, as well as the potassium and sodium salts thereof.

The esters according to the invention are not only interesting active compounds but particularly they are important intermediates for the preparation of the acid as well as the salts.

Furthermore, a process for the preparation of the substituted alkenoic acid derivatives of the general formula (I)

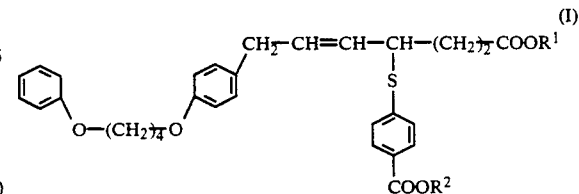

wherein $R^1$, $R^2$ have the abovementioned meaning, has been found, which is characterized in that

[A] aldehydes of the general formula (II)

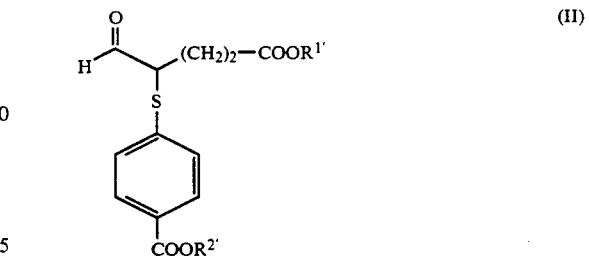

wherein $R^{1'}$, $R^{2'}$ are identical or different and denote branched or straight-chain $C_1$-$C_6$-alkyl or benzyl, are reacted with phosphorous compounds of the general formula (III)

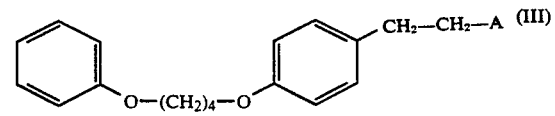

wherein A represents a group of the formula

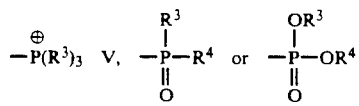 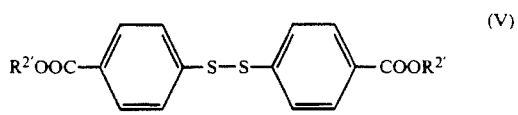

in which $R^3$, $R^4$ are identical or different and denote phenyl or $C_1$–$C_6$-alkyl, and V denotes a halide anion or a tosylate anion, in inert solvents in the presence of bases, or

[B] hydroxy alkenoic acid derivatives of the general formula (IV)

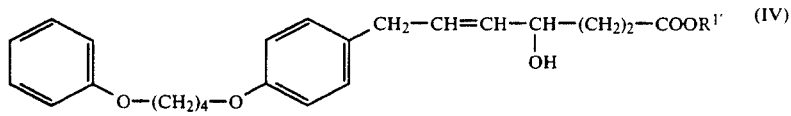

wherein $R^{1'}$ has the abovementioned meaning, are reacted with disulfides of the general formula (V)

where $R^{2'}$ has the abovementioned meaning, in inert solvents in the presence of a reducing agent and in the case of the preparation of the acid ($R^1$, $R^2$=H) the esters are then hydrolysed or partially hydrolysed, and in the case of the preparation of the salts, the acid is reacted with the appropriate base.

The process according to the invention can be illustrated by the following equation:

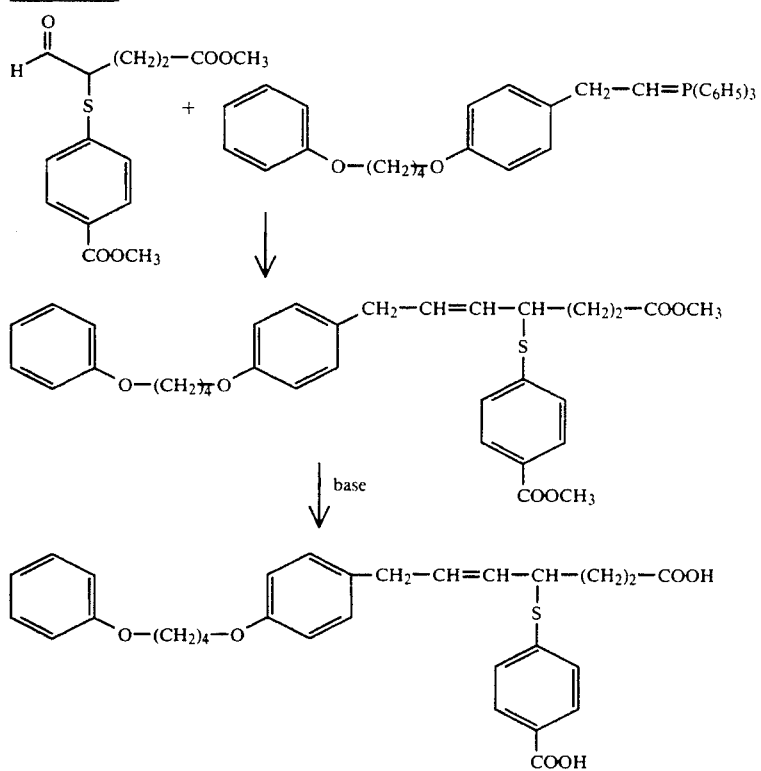

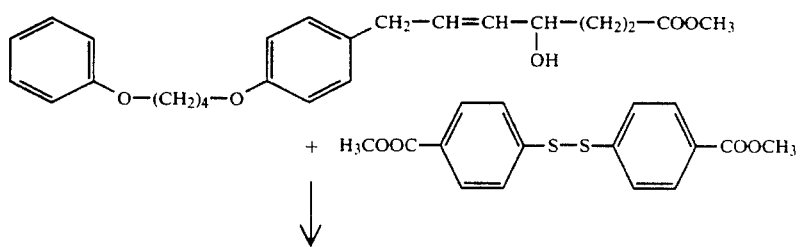

-continued

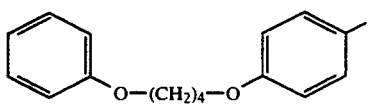 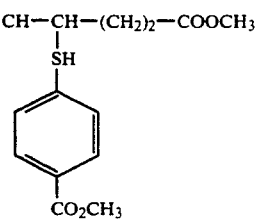

Process Variant [A]

Halide anions are preferably chlorides, bromides or iodides.

Suitable inert solvents for the process (variant A) according to the invention are those conventional organic solvents which do not change under the reaction conditions. They preferably include ethers such as diethyl ether, butyl methyl ether, dioxane, tetrahydrofuran, glycol dimethyl ether or diethylene glycol dimethyl ether, or hydrocarbons such as benzene, toluene, xylene or petroleum fractions, or amides such as dimethylformamide or hexamethylphosphoric triamide, or 1,3-dimethyl-imidazolidin-2-one, 1,3-dimethyl-tetrahydro-pyridimin-2-one or dimethyl sulphoxide. It is likewise possible to use mixtures of the solvents mentioned.

Suitable bases are the conventional basic compounds for basic reactions. These preferably include alkali metal hydrides such as, for example, sodium hydride or potassium hydride, or alkali metal alcoholates such as sodium methanolate, sodium ethanolate, potassium methanolate, potassium ethanolate or potassium tert.-butylate, or amides such as sodium amide or lithium-diisopropylamide, or organolithium compounds such as phenyllithium, butyllithium or methyllithium or sodium hexamethyldisilazane or potassium hexamethyldisilazane.

The choice of solvent or base depends on the stability, sensitivity to hydrolysis or CH acidity of the respective phosphorous compound. Ethers such as diethyl ether, tetrahydrofuran, dimethoxyethane or dioxane, together with a co-solvent such as dimethylformamide or 1,3-dimethyl tetrahydropyridimin-2-one or 1,3-dimethylimidazolid-2-one, are particularly preferably used as solvent. Alkali metal alcoholates such as potassium tert.-butylate, or organolithium compounds such as phenyllithium or butyllithium or sodium hydride are particularly preferably used as bases.

The reaction is generally carried out in the temperature range from −80° C. to +70° C., preferably from −80° C. to +20° C.

The reaction may be carried out at atmospheric, elevated or reduced pressure (for example 0.5 to 5 bar). In general, the reaction is carried out at atmospheric pressure.

When carrying out the reaction the phosphorous compounds are generally employed in an amount of from 1 to 2 moles, preferably in molar amounts, relative to 1 mole of the aldehyde. The bases are generally employed in an amount of from 1 to 5, preferably from 1 to 2 moles, relative to 1 mole of the phosphorous compound.

The process (variant A) according to the invention can be carried out for example by adding the base and then the aldehyde, if appropriate in a suitable solvent, to the phosphorous compounds dissolved or suspended in a suitable solvent, and if appropriate, heating the mixture. The working up is effected in a conventional manner by extraction, chromatography and/or crystallization.

When carrying out the process (variant A) according to the invention, it is likewise possible to employ the appropriate phosphoranes which have previously been prepared from the appropriate phosphonium salts and bases in a separate reaction, directly in place of the phosphonium salts. However, it has proven favourable to carry out the reaction with the phosphorous compounds in the presence of bases as a one-pot process.

Process Variant [B]

Compounds of the general formula I may be prepared from compounds of formula IV by reaction of the latter with disulphides (V) in the presence of a trialkyl phosphine, to liberate a nucleophilic sulphur compound, in a suitable inert solvent. The reagents are further activated to nucleophilic displacement by performing the reaction in the presence of a suitable base. The reaction is preferably carried out between −20° C. and 35° C. A particularly preferred temperature range is 0° to 5° C. Preferred bases are tertiary amines. A particularly preferred base is pyridine. Preferred trialkylphosphines are triphenylphosphine or tributylphosphine with the latter reagent being particularly preferred. Suitable solvents are pyridine, benzene, tetrahydrofuran and acetonitrile. Acetonitrile and pyridine are particularly preferred solvents. Both disulphide and trialkylphosphine are used in equimolar proportions preferably in a ratio of two to one of alcohol (IV). An excess of the base employed is used with a five to one molar ratio being particularly preferred. This process proceeds stereospecifically with inversion of the chiral centre.

To prepare the carboxylic acid ($R^1$, $R^2$=H) according to the invention, the carboxylic acid esters are in general hydrolysed by customary methods. The hydrolysis in general takes place by treating the esters in inert solvents with customary bases, by means of which in general the salts of the carboxylic acid, are formed first, which can subsequently then be converted, probably in a second step, into the free carboxylic acid of the formula (I) by treating with acid.

Bases suitable for the hydrolysis are the customary bases. These preferably include alkali metal hydroxides or alkaline earth metal hydroxides such as, for example, lithium hydroxide, sodium hydroxide, potassium hydroxide or barium hydroxide, or alkali metal carbonates such as sodium carbonate or potassium carbonate or sodium hydrogen carbonate, or alkali metal alkoxides such as sodium ethoxide, sodium methoxide, potassium methoxide, potassium ethoxide or potassium tert.-butoxide. Sodium hydroxide, potassium hydroxide or lithium hydroxide are particularly preferred.

Suitable solvents for the hydrolysis are water or the organic solvents which are customary for hydrolysis.

These preferably include alcohols such as methanol, ethanol, propanol, isopropanol or butanol, or ethers such as tetrahydrofuran or dioxane, or dimethylformamide or dimethyl sulphoxide. Ethers such as tetrahydrofuran or dioxane are particularly preferably used. Likewise, it is possible and preferable to employ mixtures of the solvents mentioned.

The hydrolysis is in general carried out in a temperature range from 0° C. to +80° C., preferably from +10° C. to +60° C.

In general, the hydrolysis is carried out at normal pressure. However, it is also possible to work at underpressure or at overpressure (for example from 0.5 to 5 bar).

When carrying out the hydrolysis, the base is in general employed in an amount from 2 to 6 moles, preferably from 2 to 6 moles, relative to 1 mole of the diester.

The phosphorous compounds of the general formula III are known. They can be prepared according to the process described in GB 2 218 416.

The aldehydes of the general formula II are new.

They can be prepared by reacting a sulfenyl chloride of the formula VI $$\text{Cl-S-}\underset{\text{COOR}^{2'}}{\text{C}_6\text{H}_4} \quad \text{(VI)}$$

wherein $R^{2'}$ has the abovementioned meaning, with a compound of the formula (VII)

$$R^5O-CH=CH-(CH_2)_2-COOR^{1'} \quad \text{(VII)}$$

wherein $R^{1'}$ has the abovementioned meaning, $R^5$ denotes $C_1$-$C_4$-alkyl, preferred methyl or ethyl, or denotes trimethylsilyl or tert.butyldimethylsilyl in inert solvents, optionally in the presence of bases.

Suitable solvents are hydrocarbons such as benzene or toluene, ethers, for example diethylether, tetrahydrofuran or dioxane, or chlorinated hydrocarbons such as methylene chloride or chloroform or mixtures of the solvents mentioned. Preferred solvents are chlorinated hydrocarbons such as methylene chloride.

The preparation optionally is carried out in the presence of bases such as triethylamine, diisopropylamine or pyridine, or sodium or potassium carbonate.

In general, the sulfenyl chloride of the formula (VI) is generated in situ (in the reaction solution) by reacting the appropriate thiol with sulfuryl chloride.

The reaction in general is carried out in a temperature range from $-78°$ C. to $+20°$ C., preferably from $-78°$ C. to $-20°$ C.

In general, the reaction is carried out at normal pressure. However, it is also possible to work at underpressure or at overpressure.

The preparation of the aldehydes can be illustrated by the following equation:

$$H_3CO-CH=CH-(CH_2)_2-COOCH_3$$

+

$$\text{Cl-S-}\underset{\text{COOCH}_3}{\text{C}_6\text{H}_4}$$

↓

$$\underset{H}{\overset{O}{\|}}\text{C}-\underset{\underset{\text{S-C}_6\text{H}_4\text{-COOCH}_3}{|}}{\text{CH}}-(CH_2)_2-COOCH_3$$

Since the compounds of the general formula (I) possess a chiral centre and therefore exist in the form of their isomers, the enantiomerically pure species can be prepared by the stereospecifically transformation of appropriate chiral precursors.

An appropriate chiral precursor may preferably be the (Z)-(4R) hydroxy compound of the formula $$\text{C}_6\text{H}_5\text{-O-(CH}_2)_4\text{-O-C}_6\text{H}_4\text{-CH}_2\text{-CH=CH-}\underset{\underset{\text{OH}}{|}}{\text{CH}}\text{-(CH}_2)_2\text{COOR}^{1'} \quad \text{(IVa)}$$

The isomers of the formula (IVa) are new and can be prepared according to the process variants illustrated by the following reaction equations:

$$X = \text{C}_6\text{H}_5\text{-O-(CH}_2)_4\text{-O-C}_6\text{H}_4\text{-}$$

Process variant C $$\text{OHC-}\underset{O}{\overset{\overset{O}{\|}}{\text{(lactone)}}} + XCH_2CH_2A \xrightarrow{C1}$$

VI     III $$X\text{-CH}_2\text{-CH=CH-}\underset{O}{\overset{\overset{O}{\|}}{\text{(lactone)}}} \xrightarrow{C2}$$

VII $$X\text{-CH}_2\text{-CH=CH-}\underset{\underset{\text{OH}}{|}}{\text{CH}}\text{-(CH}_2)_2\text{COOH} \xrightarrow{C3} \text{IVa}$$

IVb

Process variant D

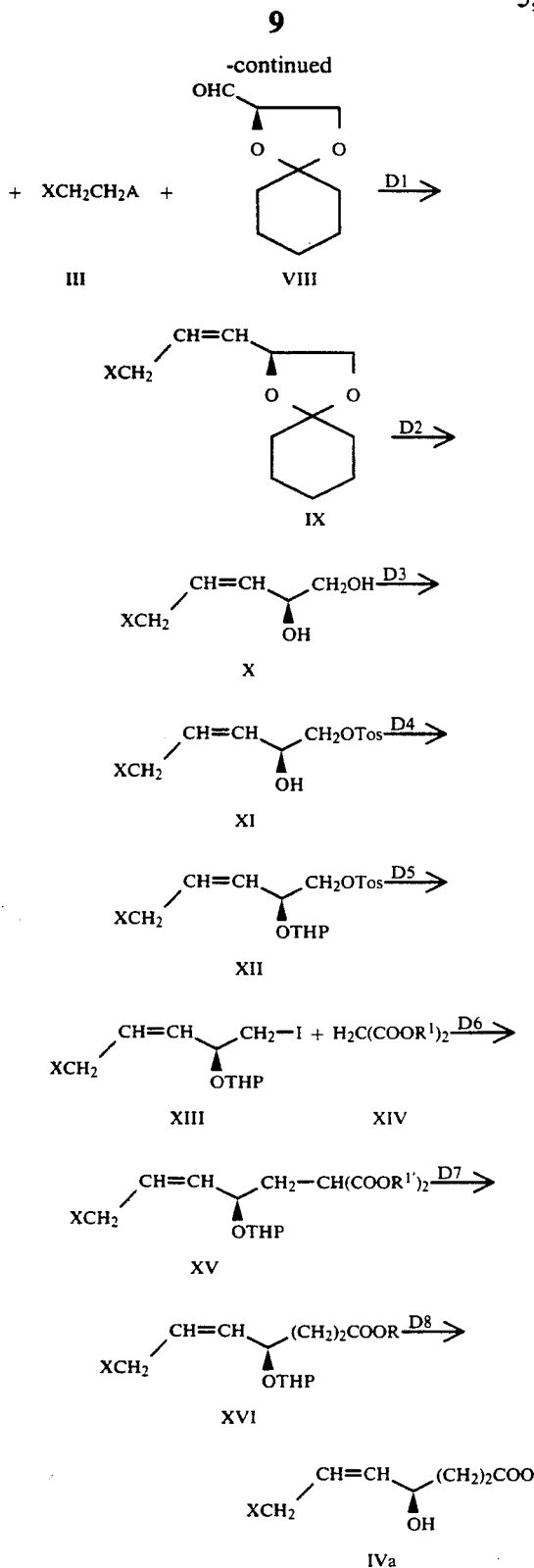

Tos = p-tolyl-sulfonyl
THP = tetrahydropyranyl.

Process variant E

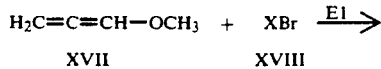

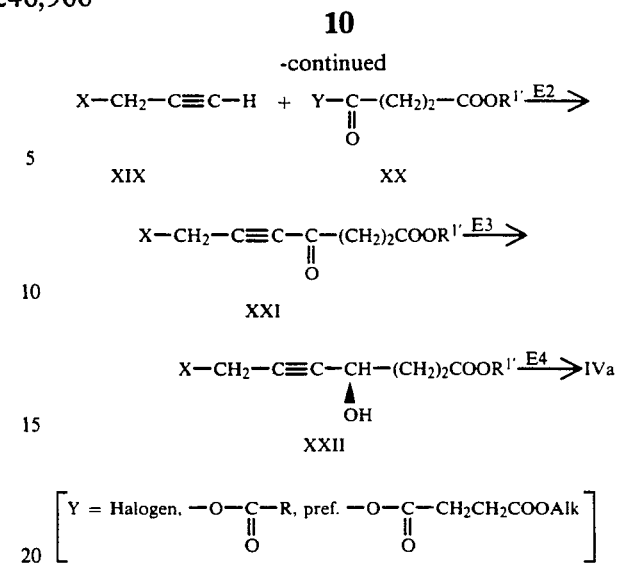

$$\begin{bmatrix} Y = \text{Halogen,} -O-\underset{\underset{O}{\|}}{C}-R, \text{ pref. } -O-\underset{\underset{O}{\|}}{C}-CH_2CH_2COOAlk \end{bmatrix}$$

Reaction Conditions of Process Variant [C]

In the first reaction step [C1] an appropriate phosphorous compound of the formula III, preferably the appropriate triphenylphosphonium bromide in the presence of a base such as butyllithium is reacted in an inert solvent such as hydrocarbons or others, preferably tetrahydrofuran or hexane, in an temperature range of $-20°$ C. to $+30°$ C., preferably from $-10°$ C. to $+10°$ C. to yield the furanone of the formula VII. In the second reaction step [C2], the furanone VII may be hydrolysed to a compound of the general formula IVb.

This is preferably performed by treatment with an alkali metal hydroxide preferably in a mixture of water and a miscible organic solvent. This process may be carried out at temperatures between $-20°$ C. and $+100°$ C. preferably at $+20°$ C. To obtain compounds of the formula (I) it is preferable to use a compound of formula (IVb) where $R^1$ is not hydrogen. Such compounds are preferably prepared by mixing of the acid with an inorganic base and a voltile lower alkyl halide in an inert solvent. A preferred base is potassium carbonate and preferred halides are methyl iodide and ethyl bromide. These are preferably mixed in a molar ratio of one:two:five. A preferred solvent is dimethylformamide and the mixture is preferably at a temperature of $+30°$ to $+40°$ C.

Alternatively, compounds of the formula I may be obtained directly from compounds of the formula VII by reaction of the latter with an anion of 4-mercaptobenzoic acid preferably the sodium thiolate. The latter is generated by treating the thiol with two components in a suitable solvent preferably at elevated temperatures. A particularly preferred solvent is dimethylformamide at a temperature of 120° C. The reagents are preferably mixed in an equimolar ratio. This reaction proceeds with inversion of stereochemistry at the chiral centre.

Reaction Conditions of the Process Variant [D]

In the first reaction step [D1] of this variant the phosphonium compound of the formula III—preferably the appropriate phosphonium salt in the presence of a base such as butyllithium—is reacted with the aldehyde of the formula VIII in inert solvents such as hydrocarbons or ethers or mixtures thereof, preferably in ethers such as dioxane or particularly preferred tetrahydrofuran, in a temperature range of from −78° C. to +20° C., preferably from −40° C. to 0° C. to give the cyclic acetal of the formula IX. In the second step [D2], the acetal IX is hydrolysed in solvents such as alcohols e.g. methanol, ethanol, or water or dioxane, or mixtures thereof, preferably in methanol, in the presence of an acid such as the usual inorganic or organic acids preferably in the presence of acetic acid, in a temperature range of from 0° C. to +120° C., preferably from +20° C. to +80° C., to give the diol of the formula X.

In the third step [D3] the primary hydroxy group of the diol X is protected by the tosyl group via the usual methods. Preferably the diol X is tosylated with p-toluene sulfonic acid chloride in an inert solvent such as halogenated hydrocarbons e.g. methylene chloride, or pyridine, preferably pyridine, in a temperature range of from −20° C. to +60° C. preferably from 0° C. to +20° C. to give compound XI which in the fourth reaction step [D4] is protected at the second hydroxy group by reacting the tosylate XI with dihydropyran, if appropriate in the presence of an acid such as toluene sulfonic acid or acetic acid, in inert solvents such as hydrocarbons, ethers or halogenated hydrocarbons, preferably in methylene chloride or chloroform, in a temperature range of from −20° C. to +60° C., preferably from 0° C. to +40° C. to give compound of the formula XII. In the fifth step [D5] the tosylate group is exchanged for the iodine group by reacting compound XII with sodium or potassium iodide in an inert solvent such as acetone in a temperature range of from 0° C. to +100° C., preferably from +20° C. to +80° C. to give the compound XIII, which then is reacted in the sixth step [D6] with malonate XIV in the presence of a base such as metal hydrides or butyllithium, preferably sodium hydride, in inert solvents such as hydrocarbons, ethers or dimethyl sulfoxide, preferably dimethyl sulfoxide, in a temperature range of from 0° C. to +150° C., preferably from +20° C. to +120° C. to give the diester XV. In the seventh step [D7] the diester XV is transferred into compound XVI by reacting with lithium chloride in dimethyl sulfoxide. In the last step [D8] compound XVI is deprotected to give the hydroxy compound IVb by hydrolysing XVII with suitable organic acids such as preferably acetic acid in solvents such as water, alcohols e.g. methanol or ethanol, and acetic acid, or mixtures thereof, in a temperature range of from +20° C. to +80° C., preferably from +20° C. to +60° C.

Reaction Conditions of Process Variant [E]

In the first step [E1] methoxy allene XVII is reacted with the bromide of the formula XVIII via a Grignard reaction with magnesium in ether such as tetrahydrofuran to give the propyne of the formula IX. In the second step [E2], the propyne IX is reacted with the succinic acid derivative XX in inert solvents such as ethers or halogenated hydrocarbons, preferably in tetrahydrofuran, in the presence of a base such as butyl lithium with or without addition of a metal salt such as ZnCl₂, CnBr, in a temperature range of from −78° C. to +40° C., preferably from −40° C. to +20° C., to give the compound of the formula XXI. In the third step [E3], compound XXI is reduced in inert solvents such as tetrahydrofuran to give the hydroxy compound XXII. In a fourth step [E4] the triple bond of compound XXII is stereoselectively partially reduced to a (Z)-double bond, yielding the alkylic alcohol compound IVa. The reduction is preferably carried out by catalytic hydrogenation, preferably using a Lindlar-type catalyst in an inert solvent such as ethyl acetate.

The chiral aldehyde VI is known and may be obtained from readily available (chiral) starting material according to known methods. [Ravid, U., Silverstein, R. M. and Smith, L. R., Tetrahedron 34, 1449 (1978); Eguchi, C. and Kakuta, A., Bull. Chem. Soc. Jap. 47, 1704 (1974); Doolittle, R. E., Tumlinson, J. J., Proveaux, A. T. and Heath, R. R., J. Chem. Ecology 6, 473 (1980)].

A particularly preferred chiral starting material to prepare the aldehyde VI is D-(or L-)glutamic acid.

The aldehyde VIII is known, or may be prepared according to known methods [M. Grauert et al., Liebigs Ann. Chem. 98, 552 (1986)].

The compounds according to the invention are pharmacologically active being leukotriene antagonists. Surprisingly they have superior properties compared with known leukotriene antagonists.

Accordingly the compounds are indicated for the therapeutic use in the treatment of diseases in which leukotrienes are implicated. These include allergic reactions of the pulmonary system in which leukotrienes are thought to be causal mediators of bronchospasm, for example, in allergic lung disorders such as extrinsic asthma and industrial asthma, and in other inflammatory disorders for example allergic skin diseases, psoriasis, contact hypersensitivity, bronchitis. Moreover, the compounds of the invention are suitable for the treatment of cardiovascular disorders such as shock and ischaemic heart diseases, for example, myocardial infarction, cerebrovascular diseases as well as renal diseases.

To evaluate the pharmacological properties the receptor affinity of the compounds were determined by measuring its ability to displace [$^3$H-LTD$_4$] binding to guinea-pig lung membranes.

Test method: [$^3$H]-LTD$_4$ BINDING ASSAY

Increasing concentrations (between $10^{-8}$ and $10^{-5}$M) of compounds of general formula I were incubated with 0.8 nM$^3$H-LTD$_4$ and guinea-pig lung membranes (100–150 μg protein) for 15 minutes at 20° C. in an assay buffer of 10 mM L-cysteine and 1% polypep in 50 mM Tris HCl at pH 7.4. Incubations (total volume 0.25 ml) were terminated by addition of ice-cold Tris HCl (pH 7.4) and rapidly filtered through Whatman GF/C filters which were washed twice with ice-cold buffer. All points were determined in triplicate.

The counts (dpm) bound to each filter were determined by liquid scintillation spectrometry. The amount bound in the presence of each concentration of test compound was compared to the amount of binding in the absence of test compound and to the amount of binding in the absence of test compound and to the amount bound in the presence of 2 μm LTD$_4$. A concentration displacement curve was then calculated by non-linear regression to give the concentration at which 50% of the displaceable binding was inhibited (IC$_{50}$). The Cheng and Prusoff correction was applied to convert this to the negative logarithm of the test compound's receptor affinity (pKi).

$$pKi = -\text{Log}\left[\frac{IC_{50}}{1 + [^3H\text{-}LTD_4]/0.8}\right]$$

Where 0.8 nM is the dissociation constant for $^3$H-LTD$_4$ under these conditions and [$^3$H-LTD$_4$] is the precise concentration (in nM) employed in the assay (also determined by liquid scintillation counting).

Compound of Example No. 4 pK$_i$
[$^3$H-LTD$_4$]
7.5

The present invention also includes pharmaceutical preparations which contain one or more compounds of the general formula I, or which consist of one or more active compounds of the formula (I) in addition to inert, non-toxic, pharmaceutically suitable auxiliaries and excipients, and a method for the production of these preparations.

The active compounds of the formula (I) are intended to be present in these preparations in a concentration of 0.1 to 99.5% by weight, preferably of 0.5 to 95% by weight of the total mixture.

In addition to the active compounds of the formula I, the pharmaceutical preparations may also contain other pharmaceutical active compounds.

The abovementioned pharmaceutical preparations can be prepared in a customary manner by known methods, for example with the auxiliary (auxiliaries) or excipient(s).

In general, it has proven advantageous to administer the active compound(s) of the formula (I) in total amounts of about 0.03 to about 30-mg/kg, preferably to about 5 mg/kg of body weight every 24 hours, if appropriate in the form of several individual doses, to attain the desired result.

An individual dose contains the active compound(s), preferably in amounts of 0.01 to about 10, particularly preferably 0.1 to 1.0 mg/kg of body weight.

However, it may be advantageous to deviate from the amounts mentioned, in particular depending on the type and the body weight of the subject to be treated, on individual behaviour towards the medicaments, the type and severity of the disorder, the type of preparation and administration, and the time or interval at which administration takes place.

EXAMPLES

Example 1/Process variant [A]

1a) Methyl 5-methoxypent-4-enoate

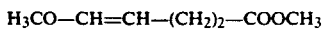

34.3 g (0.1 mole) methoxymethyltriphenylphosphonium chloride was suspended in 100 ml dry tetrahydrofuran and cooled to −78° C. under argon. 75 ml (0.1 mole) n-butyllithium solution in hexane was added and the solution allowed to warm to room temperature. After cooling to −78° C. 12.1 g (0.0105 moles) methyl 4-oxobutanoate was added in 50 ml tetrahydrofuran. The solution was allowed to reach room temperature then poured into water and extracted twice with ether. The ether extracts were washed with saturated sodium chloride solution dried and concentrated in vacuo. This was eluted through 250 g silica gel with 1 l ether-hexane 1:1 to give a faintly yellow liquid 9.2 g containing both (Z) and (E) enol ethers.

Yield: 64% of theory
NMR (CDCl$_3$, 60 MHz): 2.3 [4] s, 3.42 (major), 3.50 (minor) [3] s, 3.60 [3] s, 4.0–5.0 [1] m, 5.4–7.0 [1] m.

1b) Methyl 4-(4-methoxycarbonylphenylthio)-5-oxopentanoate

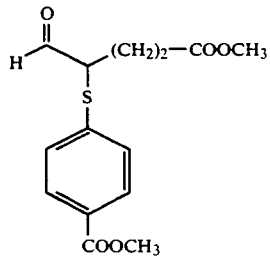

4.6 g (13.8 mmoles) of the 4,4′biscarbomethoxydiphenyl-disulphide was dissolved in 100 ml dry dichloromethane and cooled to −78° C. under argon. 1.1 ml (13.8 mmoles) sulphuryl chloride was added and the solution allowed to warm to −10° C. then again cooled to −78° C. 3.96 g (27.6 mmoles) methyl 5-methoxypent-4-enoate was then added. After warming to room temperature the solution was poured into saturated sodium bicarbonate solution. The organic layer was washed with saturated sodium chloride solution, dried and concentrated to give an orange oil which was dissolved in ether-light petroleum and on storing at −20° C. overnight deposited crystals of the disulphide which were removed by filtration.

The filtrate was chromatographed on 200 g silica gel with ether-light petroleum 1:2 eluting first disulphide then the title aldehyde as a mobile yellow oil 3.9 g.

Yield: 47% of theory
RF-value: 0.40 (ether)
NMR (CDCl$_3$, 60 MHz): 2.15 [2] dt, J = 1 Hz, 2.50 [2] t, J = 6 Hz, 3.35 [1] d, J = 3 Hz, 3.60 [3] s, 7.25 [2] d, J = 8 Hz, 7.75 [2] d, J = 8 Hz, 9,32 [1] d, J = 3 Hz.

1c) Methyl 4-(4-methoxycarbonylphenylthio)-7-(4-[4-phenoxybutoxy]phenylhept-5(Z)enoate

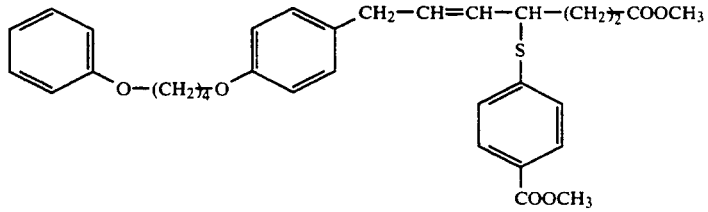

20.6 g (33.6 mmoles) 2-(4-[4-phenoxybutoxy]phenyl)ethyltriphenyl phosphonium bromide was suspended in 150 ml dry tetrahydrofuran and 21 ml (33.6 mmoles) n-butyllithium in hexane was added under argon. This was stirred for 15 min at room temperature and cooled to −78° C. 9.1 g (30.7 mmoles) methyl 4-(4-methoxycarbonylphenylthio)-5-oxopentanoate was added in 50 ml tetrahydrofuran. After warming to room temperature the solution was poured into water and extracted twice with ether. The ether extracts were washed with saturated sodium chloride then dried and concentrated in vacuo to give a brown oil. This was subjected to flash chromatography on 200 g silica with ether-hexane 1:1 as the eluent to give 10.4 g impure product.

Recrystallisation from ethyl acetate-hexane gave white needles m.p. 63°-64° C., 2.97 g. The residue was subjected to medium-pressure liquid chromatography on 300 g silica with ether-hexane 15/85. Recrystallisation of the purified material gave an additional 3.34 g m.p. 62°-63° C.

Yield: 37.5% of theory
RF Value: 0.16 (ether-hexane 1:2)
HPLC retention time: 12.30 min Lichrosorb RP-18 7 μm, 25×4 mm, acetonitrile: water: 90:10:1 ml/min, 280 nm.
NMR (CDCl$_3$, 60 MHz): 1.8-2.2 [6] m, 2.46 [2] d, J=7 Hz, 3.17 [2] d, J=7 Hz, 3.61 [3] s, 3.62 [1] t, J=5 Hz, 3.85 [3] s, 3.9-4.1 [4] m, 5.1-5.7 [2] m, 6.6-7.0 [7] m, 7.1-7.3 [2] m, 7.35 [2] d, J=8 Hz, 7.85 [2] d, J=8 Hz.

1d) 4-(4-methoxycarbonylphenylthio)-7-(4-[4-phenoxybutoxy]phenyl)hept-5(Z)enoic acid

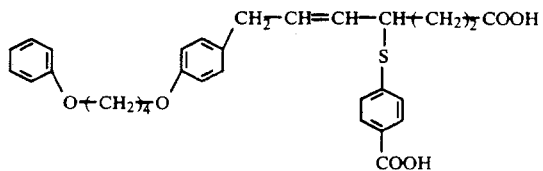

2.97 g (5.4 mmoles) methyl 4-(4-methoxycarbonylphenylthio)-7-(4-[4-phenoxybutoxy]phenyl)hept-5-(Z)enoate was dissolved in 60 ml tetrahydrofuran and stirred under argon for 64 h with 5.0 g (0.2 moles) lithium hydroxide in 30 ml water. The organic solvent was removed in vacuo and the aqueous solution acidified with 1M hydrochloric acid. The resulting white precipitate was collected by filtration, washed with water and dried in vacuo overnight giving a white powder 2.61 g m.p. 151°-3° C.

Yield: 92.6% of theory
U.V. (MeOH): λmax 278.9 nm, ε8800
HPLC retention time: 3.92 min, Lichrosorb RP-18 7 μm 25×4 mm, acetonitrile: water: acetic acid 90:10:0.1 adjusted to pH 5.6 with ammonia, 1.0 ml/min 280 nm.
NMR (CDCl$_3$/CD$_3$OD, 60 MHz): 1.8-2.1 [6] m, 2.35 [2] t, J=6 Hz, 2.47 [2] t, J=6 Hz, 3.1 [2] d, J=7 Hz, 3.8-4.1 [5] m, 5.1-5.7 [ ] m, 6.6-7.0 [7] m, 7.1-7.3 [2] m, 7.36 [2] d, J=7.86 [2] d, J=8 Hz.

Example 2/Process variant [B]

2a) (R)-γ-Butyrolactone-γ-carboxylic acid

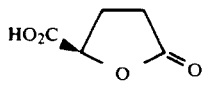

This was synthesised from R-glutamic acid, according to the literature[1]. The compound was obtained as a shite solid, m.p. 65°-67° C.

[α]$_D$ —13° (Ethanol, c 1)
NMR (d$_6$-Acetone, 60 MHz): 2.1-2.9 [4]m, 4.9-5.2 [1]m, 9.85 [1]s.

2b) R-γ-Butyrolactone-γ-carboxylic acid chloride

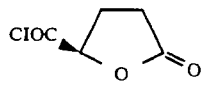

(R)-γ-butyrolactone-γ-carboxylic acid was treated with either oxalyl chloride or thionyl chloride, according to the literature[2,3], to give the corresponding acid chloride as a colourless mobile liquid, b.p. 106°-109° C. (0.85 mbar).

[α]$_D$ —55° (Benzene, c 1)
NMR (CDCl$_3$, 60 MHz): 2.2-3.2 [4]m, 5.1-5.35[1]m.

2c) (R)-γ-Butyrolactone-γ-carboxyaldehyde

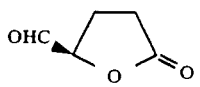

(R)-γ-butyrolactone-γ-carboxylic acid chloride on treatment with hydrogen and a catalyst such as palladium on barium sulphate in the presence of a moderator such as 1,1,3,3-tetramethylthiourea afforded the corresponding aldehyde as a colourless mobile oil, b.p. 86°-89° C. (0.4 mbar).

NMR (CDCl$_3$, 60 MHz): 2.2-2.8 [4]m, 4.75-5.05 [1]m, 9.75 [1]s.

2d) (R)-5-{3-(4-[4-phenoxybutoxy]phenyl)prop-1(Z)-enyl}dihydro-2(3H)-furanone.

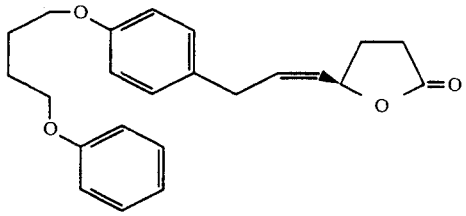

155 g (0.25 moles) 2-(4-[4-phenoxybutoxy]phenyl) ethyltriphenyl phosphonium bromide was dissolved in 1.75 l hot dry tetrahydrofuran then cooled to 25°-30° C. prior to the addition of 100 ml (0.25 moles) n-butyllithium in hexane under argon. The reaction was immediately cooled to 0° C. and 32 g (0.28 moles) R-γ-butyrolactone-γ-carboxyaldehyde was added 75 ml dry tetrahydrofuran. After 15 min at 0° C. the reaction was quenched in 500 ml saturated ammonium chloride and extracted with diethyl ether. The ether extracts were washed with saturated sodium chloride, separated and dried over magnesium sulphate then concentrated in vacuo. The crude product was taken up in 400 ml methanol and left to crystallise at 0° C. This afforded the title compound (contaminated with approximately 10% E isomer) as a white solid 50.5 g m.p. 74°-77° C.

Yield: 55.2% of theory.
[α]$_D$ —42.3° C. (Chloroform c 1.3)
HPLC retention time: 24 min. Chiral Cel OD, ethanol: hexan 30:70 0.5 ml/min, 270 nm.
NMR (CDCl$_3$, 60 MHz): 1.65-2.7 [8]m, 3.35 [2] d J=6 Hz, 3.7-4.2 [4]m, 5.0-5.95 [3]m, 6.6-7.45 [9]m.

2e) 4(R)-Hydroxy-7-(4-[4-phenoxybutoxy]phenyl)-hept-5(Z)-enoic acid

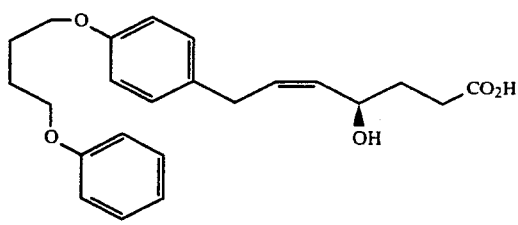

17.5 g (47.9 mmoles) (R)-{3-(4[4-phenoxybutoxy]-phenyl)prop-1-(Z)-enyl}dihydro-2-(3H)-furanone was dissolved in 100 ml dry tetrahydrofuran and 14 g (0.25 moles) potassium hydroxide added in 400 ml water. After stirring at room temperature for 17 h 500 ml ethyl acetate was added and then acidified to pH 1 with 1M hydrochloric acid. The ethyl acetate phase was combined with an additional 100 ml ethyl acetate following re-extraction of the aqueous phase and these were additionally washed with saturated sodium chloride, separated, dried over magnesium sulphate and concentrated in vacuo. Crystallisation from chloroform-hexane (3:1) gave a white solid 15 g m.p. 105°–107° C.

Yield: 82% of theory $[\alpha]_D + 14.4°$ (Chloroform c 2)

NMR (CDCl$_3$+d$_6$-DMSO, 60 MHz): 1.6–2.1 [6]m, 2.4 [2]t J=7 Hz, 3.35 [2]d J=6 Hz, 3.8–4.2 [4]m, 4.3–4.8 [1]m, 5.4–5.7 [2]m, 6.6–7.4 [9]m.

2f) Ethyl 4 (R)-hydroxy-7-(4-[4-phenoxybutoxy]-phenyl)-hept-5-(Z)-enoate.

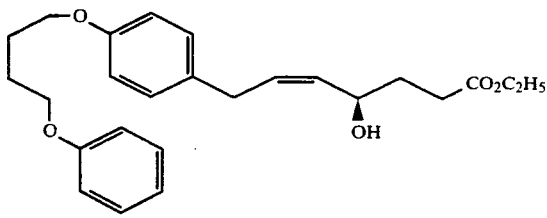

20.8 g (54 mmoles) 4(R)-hydroxy-7-(4-[4-phenoxybutoxy]phenyl)-hept-5(Z)-enoic acid, 15.2 g (112 mmoles) anhydrous potassium carbonate and 20 ml (270 mmoles) bromoethane in 200 ml dry dimethylformamide were heated at 35° C. for 24 h. The mixture was cooled and filtered and the filtrate diluted with 400 ml water and extracted with 700 ml ethyl acetate. The ethyl acetate extract was washed with saturated sodium chloride, separated, dried over magnesium sulphate and concentrated in vacuo.

Yield 97% of theory.

$[\alpha]_D + 16.1°$ (Chloroform c 1)

HPLC retention time 15.6 min ChiralCel OD, ethanol:hexane 30:70 0.5 ml/min, 270 mm.

NMR (CDCl$_3$, 60 MHz): 1.22 [3]t J=7 Hz, 1.8–2.1 [6]m, 2.3–2.5 [2]m, 2.85 [1]d J=4 Hz, 3.35 [2]d J=6 Hz, 3.9–4.1 [4]m, 4.1 [2]q J=7 Hz, 4.4–4.8 [1]m, 5.4–5.8 [2]m, 6.7–7.4 [9]m.

2g) Ethyl 4(S)-(4-methoxycarbonylphenylthio)-7-(4-[4-phenoxybutoxy]phenyl)-hept-5(Z)-enoate.

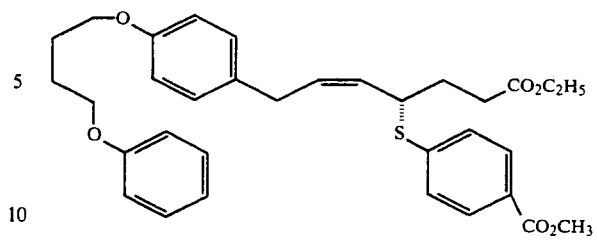

20.6 g (50 mmoles) ethyl 4(R)-hydroxy-7-(4-[4-phenoxybutoxy]phenyl)-hept-5-(Z)enoate 33.4 g (100 mmoles) 4,4'-biscarbomethoxydiphenyl-disulphide and 20 ml (250 mmoles) dry pyridine in 400 ml dry acetonitrile were cooled to 0° C. and 25 ml (100 mmoles) tributylphosphine added slowly. The mixture was stirred at 0° C. for 3 h then 50 ml toluene was added and the mixture concentrated in vacuo. The mixture was dissolved in 100 ml toluene, concentrated in vacuo, then triturated with 300 ml methanol to give a white precipitate. This was collected by filtration and crystallised from ethyl acetate-hexane (1.4) to give a white solid 19.2 g, m.p. 90.5°–91° C.

Yield: 66% of theory.

$[\alpha]_D + 42.9°$ (Chloroform c 1.1)

NMR (CDCl$_3$, 60 MHz): 1.21 [3]t J=7 Hz, 1.8–2.2 [6]m, 2.3–2.5 [2]m, 3.2 [2]d J=6 Hz, 3.85 [3]s, 3.9–4.1 [4]m, 4.10 [2]J=zHz, 4.0–4.2 [1]m, 5.1–5.8 [2]m, 6.7–7.0 [7]m, 7.1–7.4 [2]m, 7.48 [2]d J=9 Hz, 7.89 [2]d J=8 Hz.

2h) 4(S)-(4-Carboxyphenylthio)-7-(4-[4-phenoxybutoxy]phenyl)-hept-5(Z)-enoic acid

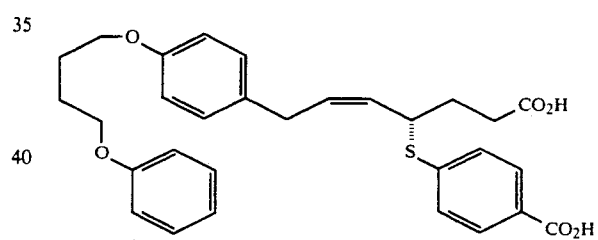

Preparation I 11.53 g (20 mmoles) ethyl 4 (S)-(4-methoxcarbonyly-phenylthio)-7-(4-[4-phenoxybutoxy]phenyl)-hept-5(Z)-enoate was dissolved in 200 ml tetrahydrofuran and 100 ml water and stirred for 40 h with 8.2 g (200 mmoles) lithium hydroxide monohydrate. The tetrahydrofuran was removed in vacuo and the solution was acidified with concentrated hydrochloric acid giving a white precipitate. This was collected by filtration, washed with water and dried overnight in vacuo then crystallised from ethyl acetate-hexane (3:1) to give a white solid 10.17 g m.p. 147°–9° C.

Yield 97.5% of theory $[\alpha]_D + 33.0°$ (Acetone, c 1)

Preparation II 5.76 g (0.24 moles) sodium hydride was suspended in 200 ml dry dimethylformamide and 18.48 g (0.12 moles) 4-mercaptobenzoic acid slowly added in 100 ml dry dimethylformamide. The mixture was heated to 100° C. and 36.6 g (0.1 mole) (R)-5-{3-(4-[4-phenoxybutoxy]-phenyl)-prop-1-(Z)-enyl}dihydro-2-(3H) furanone in 100 ml dry dimethylformamide was added. The reaction was heated at 120° C. for 4 h then poured into 410.2M hydrochloric acid. The resulting precipitate was collected and washed well with water and dried in vacuo to give 51 g crude product. This was crystallised from ethanol to give the title compound.

4(S)-(4-Carboxyphenylthio)-7-(4-[4-phenoxybutoxy]-phenyl)-hept-5(Z)-enoic acid, disodium salt.

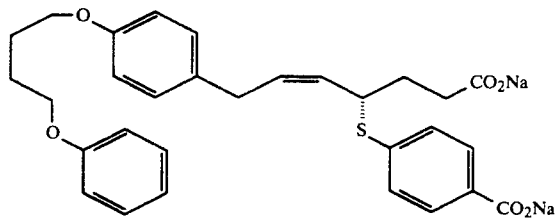

89 mg (0.17 mmoles) 4(S)-(4-carboxyphenylthio)-7-(4-[4-phenoxybutoxy]phenyl)-hept-5(Z)-enoic acid was dissolved in 343 μl of 1M sodium hydroxide and the solution freeze dried to give a white solid 100 mg, m.p. >260° C.

Yield: 100% of theory
$[\alpha]_D + 44.1°$ (Dimethyl sulphoxide c 0.54)

Example 3/Process variant [C]

3a) Z-[2S]-2-{3-[4-Phenoxybutoxy)phenyl]-1-propenyl}-1,4-dioxaspiro [4.5] decane

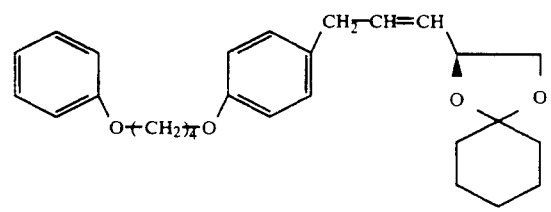

37.1 g (60.8 mmoles) 2-[4-(4-phenoxybutoxy)phenyl]ethyltriphenylphosphonium bromide were suspended in 300 ml dried THF and the mixture was cooled down to −30° C. under an atmosphere of argon. At this temperature the equivalent amount of a 1.6M solution of n-butyllithium in hexane (38 ml) plus a 4 ml excess were added with stirring (the first 4 ml did not yield a persisting orange colour of the suspension). The almost clear, deeply orange solution was stirred for another 30 min at this temperature, then cooled to −78° C. 8.64 g (50.8 mmoles) R-cyclohexylidene glyceraldehyde, dissolved in 90 ml THF, were added dropwise. After 30 min of stirring at this temperature, the reaction mixture was allowed to warm up to 0° C. in an ice/water bath. After 15 min at 0° C. the resulting suspension was poured onto ca. 100 ml hexane and treated with icewater. After decantation and filtration from a slimy precipitate, the organic phase was separated and dried over sodium sulphate. On solvent evaporation, triphenylphosphinoxide started to precipitate and was filtered off. The filtrate was further reduced in volume on a rotary evaporator and the residue was flash-chromatographed on silica gel in toluene/ethyl acetate 60:1. After evaporation, the title compound was obtained as a crystallizing oil.

Yield: 18.3 g (85%) R$_f$ (SiO$_2$, toluene/ethyl acetate 20:1): 0.30

3b) Z-[2S]-5-[4-(4-Phenoxybutoxy)phenyl]-3-pentene-1,2-diol

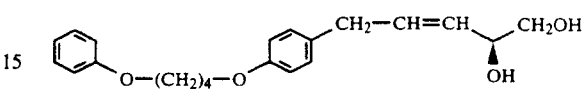

214 g (0.51 moles) of the compound of example 3a) were stirred in 1.21 methanol with 400 ml 60% (v/v) acetic acid at 60° C. for ca. 60 h, resulting in complete solution. After cooling, the formed precipitate was filtered off, washed with methanol/water 8:1 and water, and dried. A second crop was isolated from the mother liquors. These were evaporated and the residue taken up again in 170 ml methanol and 60 ml 60% acetic acid and the mixture was stirred at 60° C. overnight. Work up was performed as outlined above. The combined precipitates were recrystallized from ethyl acetate. Fractions with m.p.≧110° and $[\alpha]_D^{20}$ (CHCl$_3$, c 1)>12 were regarded as pure enough for further use. From the experiment described above thus were obtained: Yield: 113 g (65%); m.p. 112, 5° C.; $[\alpha]_D^{20}$ (CHCl$_3$, c=1.01)=13.3.

3c) Z-[2S]-5-[4-(4-Phenoxybutoxy)phenyl[-1-tosyloxy-3-penten-2-ol

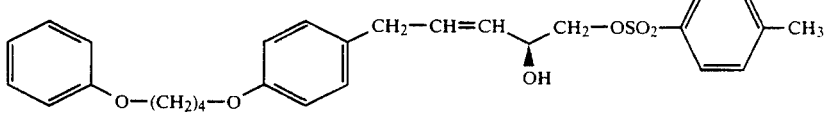

2.10 g (6.13 mmoles) of the compound of example 3b) were dissolved in 30 ml pyridine and cooled to 0° C. in an ice/water bath. 1.16 g (6.13 mmoles) p-toluenesulfonyl chloride and a few crystals of N,N-Dimethyl-4-aminopyridine (DMAP) were added and the mixture was stirred at this temperature for several days. After addition of another 0.22 g (1.16 mmoles) p-toluenesulfonyl chloride and stirring overnight, the reaction was stopped despite incomplete conversion (TLC-control in toluene/ethyl acetate 1:1).

A little ice was added, the solvent evaporated in vacuo, the residue taken up in toluene for several times and reduced in volume again. The final residue was dissolved in ethyl acetate, washed with water three times, dried over sodium sulphate and the solvent evaporated. The resulting crude product was purified by flash chromatography on silica gel in toluene/ethyl acetate 5:1. Yield: 2.44 g (80%) title compound as a crystallizing oil. R$_f$ (SiO$_2$, toluene/ethyl acetate 3:1): 0.40.

3d) Z-[4S]-1-[4-(4-Phenoxybutoxy)phenyl)]-4-tetrahydropyran-2-yloxy)-5-tosyloxy-2-pentene

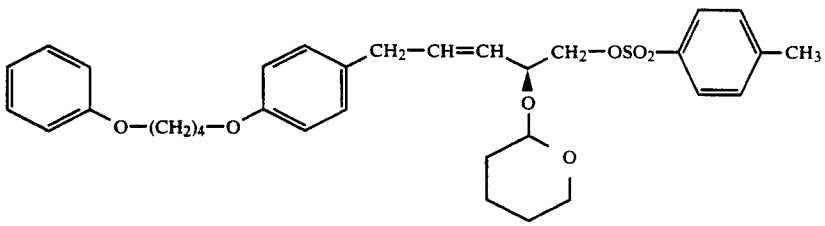

11 g (22 mmoles) of the compound of example 3c) in 150 ml dichloromethane were treated with 2.0 ml (22 mmoles) dihydropyran and 0.33 g p-toluenesulfonic acid. After stirring at room temperature for 4 h and TLC-control on silica gel in toluene/ethyl acetate 5:1, another 0.40 ml (4.4 mmoles) dihydropyran were added and stirring was continued overnight. Complete conversion was not achieved. The reaction mixture was washed with 10% aqueous sodium bicarbonate for several times, dried over sodium sulphate, and the solvent was evaporated in vacuo. Threefold crystallization from ether yielded 4.0 g (29%) of the title compound. From the mother liquors were obtained by chromatography on silica gel in toluene/ethyl acetate 40:1 another. 4.7 g (34%, total yield 63%) of the title compound together with ca. 1.7 g (ca. 15%) starting material R$_f$ (SiO$_2$, toluene/ethyl acetate 20:1): ca. 0.21, two isomers.

3c) Z-[4S]-5-Iodo-1-[4-(4-phenoxybutoxy)phenyl]-4-(tetrahydropyran-2-yloxy)-2-penten

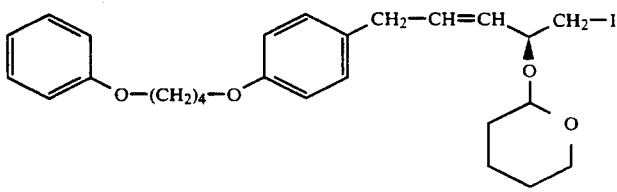

4.7 g (7.7 mmoles) of the compound of example 3d) were dissolved in acetone and refluxed overnight after addition of 1.7 g (11 moles) anhydrous sodium iodide (TLC-control on silica gel in toluene/ethyl acetate 10:1). The same amount of sodium iodide was added again and heating continued for 60 h, another 4 g sodium iodide was added and refluxing resumed overnight. After cooling, the solvent was evaporated, the residue taken up in ethyl acetate and the suspension washed with water. The organic phase was dried over sodium sulphate. The crude product was freed from solvent in vacuo and chromatographed on silica gel in toluene. Yield: 3.0 g (74%) R$_f$(SiO$_2$, toluene/ethyl acetate 10:1): ca. 0.42, two isomers.

3f) Z-[2R]-2-{5-[4-(4-Phenoxybutoxy)-phenyl]-2-(tetrahydropyran-2-yloxy)-3-pentenyl}-propanedioic acid dimethyl ester

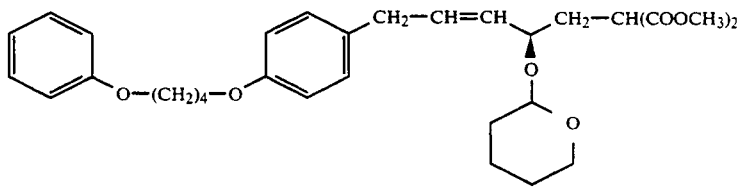

To a suspension of 0.129 g (4.28 mmoles) sodium hydride (80% in white oil) in ca. 4 ml DMSO were added dropwise 0.495 ml (4.33 mmoles) dimethyl malonate. After the initially vigorous gas evolution had ceased, the mixture was warmed to 50° C. and 1.95 g (3.64 mmoles) of the compound of example 3e), dissolved in 8 ml DMSO, were added.

Then the reaction mixture was heated to 120° C. for about 30 min (TLC control on silica gel in toluene/ethyl acetate 20:1). After cooling, icewater was added and the mixture extracted with ether for several times. The combined organic phases were washed with water (three times) and with brine, then dried over sodium sulphate. The crude product resulting from evaporation of the ether was purified by flash-chromatography on silica gel in toluene/ethyl acetate 40:1. Yield: 1.40 g (71%); R$_f$(SiO$_2$, toluene/ethyl acetate 5:1); Isomer A: 0.57; Isomer B: 0.54.

3g) Methyl Z-[4S]-7-[4-(4-Phenoxybutoxy)-phenyl]-4-tetrahydropyran-2-yloxy)-5-heptenoate

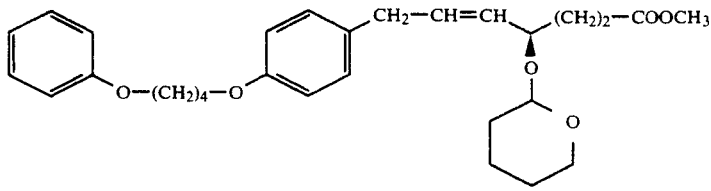

1.4 g (2.6 mmoles) of the compound of example 3f) were heated to 140° C. for 12 h in 15 ml DMSO with 0.22 g (5 mmoles) lithium chloride and 46 μl (2.6 mmoles) water (TLC control on silica gel in petroleum ether-/ethyl acetate 5:1). After cooling to room temperature, icewater was added and the mixture repeatedly extracted with ether. The combined ether layers were washed with water and with brine, dried over sodium sulphate and evaporated to dryness. The resulting crude product was purified by chromatography on silica gel in petroleum ether/ethyl acetate 10:1. Yield: 0.77 g (62%); $R_f$ (SiO$_2$, petroleum ether/ethyl acetate 5:1): ca. 0.15, two isomers.

3h) Methyl Z-[4R]-4-Hydroxy-7-[4-(4-phenoxybutoxy)phenyl)-5-heptenoate acid dimethyl ester were stirred in ca. 120 ml dried pyridine under an atmosphere of argon. 6.8 g (8.4 ml, 34 mmoles) tri-n-butylphosphine were added dropwise at room temperature and stirring of the resulting orange yellow solution was continued for 3 h. Another 1.6 g (7.9 mmoles) tri-n-butylphosphine were added and stirring was continued overnight. After evaporation of the solvent in vacuo, the residue was triturated with toluene and the solution concentrated to dryness again.

The resulting crude product was purified by chromatography on silica gel (toluene/ethyl acetate 200:1) followed by crystallization from methanol. Yield: 5.56 g (60%); purity 96% (HPLC); $R_f$ (SiO$_2$, toluene/ethyl acetate 20:1): 0.28; m.p. 89° C. $[\alpha]_D^{20}=43.6$ (c=0.505, CHCl$_3$).

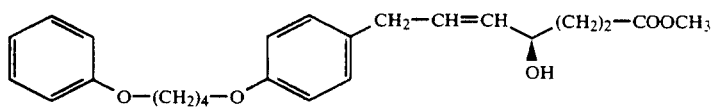

0.344 g (0.713 mmoles) of the compound of example 3g) were suspended in 10 ml 60% (v/v) acetic acid with a 3j) Z-[4S]-4-(4-Carboxyphenylthio)-7-[4-(4-phenoxybutoxy)-phenyl]-5-heptenoic acid

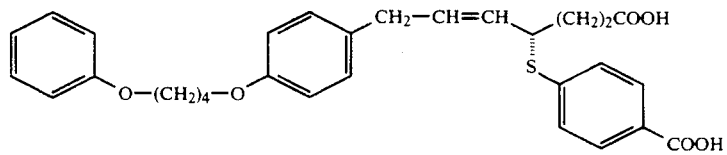

few drops of methanol and warmed to 50° C. After 45 min, most of the substance had dissolved and conversion was about complete (TLC control on silica gel in toluene/ethyl acetate 5:1). After diluting with water and extracting with ether for several times, the combined organic layers were washed with water and with brine and were dried over sodium sulphate. After evaporation of the solvent in vacuo, the residue was repeatedly taken up in toluene and evaporated to dryness again.

The resulting crude product was purified by chromatography on silica gel in toluene/ethyl acetate 20:1. Yield: 0.207 g (73%); $R_f$ (SiO$_2$, toluene/ethyl acetate 5:1): 0.15; m.p. 59.5° C.; $[\alpha]_D^{20}=12.3$ (c=1.0 in CHCl$_3$).

3i) Methyl Z-[4S]-4-(Methoxycarbonylphenylthio)-7-[4-(4-phenoxybutoxy)-phenyl]-5-heptenoate 0.40 g (0.73 mmoles) of the compound of example 3i) were heated to reflux in 20 ml THF with 3.4 ml 1N sodium hydroxide for 5 h (TLC control on silica gel in toluene/ethanol 1:1). After cooling the mixture was acidified with 1N hydrochloric acid and extracted with ethyl acetate for several times. The organic layers were washed with water and with brine, then dried over magnesium sulphate and taken to dryness on a rotary evaporator.

The resulting 0.37 g (98%) dicarboxylic acid were dissolved in ethyl acetate and reprecipitated by addition of n-hexane and dried in vacuo. Yield: 0.33 g (87%); $R_f$(SiO$_2$, toluene/ethanol 5:1):0.25; m.p. 146° C.; $[\alpha]_D^{20}=32.8$ (c=0.94, acetone).

The enantiomeric purity of the product was confirmed after reesterification with diazomethane by

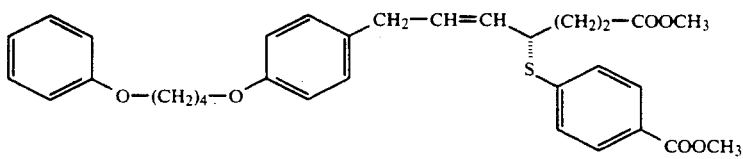

6.71 g (16.8 mmoles) of the compound of example 3h) and 11.2 g (33.6 mmoles) 4,4'-disulfanediyldibenzoic HPLC on a chiral stationary phase (Chiralcel OC, n-

Hexane/2-propanol 80:20, 1.5 ml/min. 32 bar, $t_R \simeq 17.5$ min; racemate: $t_R \simeq 14.5$ min, 17.5 min). The disodium salt was prepared by dissolving the diacid in tetrahydrofuran, treatment with the theoretical volume of 1N sodium hydroxide, dilution with water, evaporation of the organic solvent in vacuo and lyophylization. Yield: quantitative.

Example 4/Process variant [D]

4a) 4-(4-Phenoxybutoxy)phenylbromide

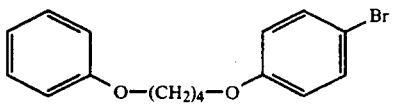

A mixture of 500 g (2.89 moles) 4-bromophenol, 661.8 g (2.89 moles) 4-phenoxybutylbromide and 400 g (2.89 moles) potassium carbonate in 3 l isopropanol is heated under reflux for 40 h. The mixture is cooled to room temperature, filtered and the precipitate is washed thoroughly with water. Drying in vacuum and recrystallizing from methanol/chloroform (600 g in 2 l MeOH/400 ml CHCl₃) yields 900 g (97%) white crystals m.p.: 79° C.

4b) 1-Methoxy-allene

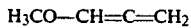

25 g (0.20 moles) Potassium-tert.-butoxide are placed in a 250 ml round-bottom flask fitted with a dropping funnel and a thermometer. 154 g (2.2 moles) Propargyl-methylether is added dropwise with magnetic stirring, the mixture is heated to reflux for about 2 h. Once the reflux temperature has dropped to 50° C., the mixture is cooled and the reflux condenser is replaced by a distillation apparatus. The product is quickly distilled to yield 148 g (95%) b.p.: 50° C.

4c) 3-[4-(4-Phenoxybutoxy)phenyl]-propyne

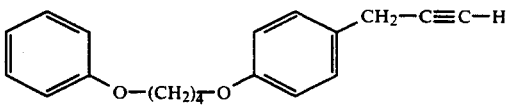

A 2 l round-bottom flask fitted with a dropping funnel, a mechanical stirrer and a thermometer is loaded with 24 g (1 mol) magnesium turnings. 200 ml freshly distilled THF are added and the apparatus is flushed with argon. After entrainment with 0.5 ml dibromoethane, a solution of 321 g (1 mol) phenoxybutyloxyphenylbromide in 1 l freshly distilled THF is slowly added, in such a way that the internal temperature stays between 50° C. and 60° C. The mixutre is heated to reflux for one hour after which it is cooled to 0° C. and carefully added to a suspension of 14.4 g (0.1 mol) CuBr in 500 ml THF and 70 g (1 mol) methoxyallene, kept below 5° C. After stirring for 1 h at 0° C., the reaction mixture was poured into 2 l aqueous ammonium chloride (10%), the aqueous layer was extracted twice with ether and the combined organic layers were washed with aqueous bicarbonate (10%) and water, dried over Na₂SO₄ and evaporated. Recrystallisation from hexane/ether yields 98 g (71%) white crystalline material (90% pure). ¹H-NMR (250 MHz, CDCl₃): $\delta = 1.95$ (m; 4H, CCH₂CH₂C), 2.15 (t, J=3H; 1H, C=C—H), 3.55 (d, J=3 Hz; 2H, Ar—CH₂—C=C), 4.00 (m; 4H, OCH₂), 6.82-7.00 (m; 5H, Ar—H), 7.30-7.45 (m; 4H, Ar—H).

4d) Methyl 7-[4-(4-phenoxybutoxy)phenyl]-4-oxa-hept-5-ynoate

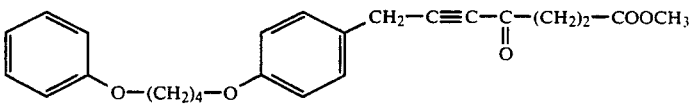

To a solution of 100 g (90% pure: 0.321 moles) compound of example 4c) in 1 l dry THF are carefully added 142 ml (0.357 moles) n-butyllithium 2.5N in hexane at −40° C. under argon. The cooling bath is removed and, after stirring for 10 min. 393 ml 1M ZnCl₂ in ether (0.393 moles) are added, while maintaining the temperature below 0° C. 65 ml Succinic acid monomethyl ester chloride (0.430 moles) are added and the mixture is stirred overnight at room temperature.

Following several extractions with saturated aqueous ammoniumchloride, the organic layers are evaporated, dissolved in acetonitrile and extracted overnight with hexanes. The acetonitrile layer is concentrated and flashchromatographed on 2 kg SiO₂ with hexanes/ether 1:1 as eluent. 54.5 g (43% based on reacted acetylene) acetylene-ketone are isolated as an amorphous yellow powder. m.p.: 62° C.; MS/CI (isobutane) e/m=395 (100%, M⁺ +1), 363 (10%, 395-MeOH).

Better yields are obtained by reacting the above mentioned lithium salt directly with succinic acid monomethyl ester anhydride which may be prepared according to the following procedure:

A mixture of 750 g succinic anhydride and 246 g methanol is stirred and heated slowly until a clear solution is formed. After heating under reflux for 30 min, 773 g acetic anhydride is added, the solution heated to reflux for 1 h and distilled under vacuum using a Vigreux distilling column. The first fraction (succinic anhydride, caution solidifies in the cooler!) is discharged.

The product is a clear, colorless oil b.p. 170° C. (2 mbar). Yield: 692 g (74%).

4e) Methyl-4-(R)-7-[4-(4-phenoxy-1-butoxy)phenyl]-4-ol-5-heptynoate

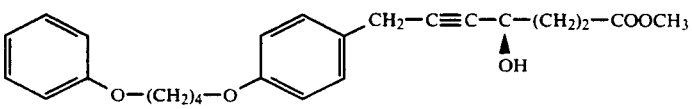

7.35 g (+)-α-Pinen (54 mmoles, e.e. >98%) is added to 100 ml 9-BBN (0.5M in THF, 50 mmoles) and the solution is refluxed for 3 h under inert gas. To the cooled solution is added 12.5 g compound of example 4d) (31 mmoles), the solution is evaporated under vacuum to about ⅓ of its original volume and stirred for 3 days at room temperature. The residue is dissolved in 150 ml acetonitrile and extracted three times with 100 ml pentane. The acetonitrile layer is concentrated and flash-chromatographed on 400 g silica (eluent: ethyl acetate:-cyclohexane 2:5). Yield: 8.44 g (61%) 91% e.e.; MS/CI (Isobutan) m/z=397 (43%, M+ +1), 365 (40%, 397-MeOH), 271 (100%, 365-OPh), 149 (60%, PhO(CH$_2$)$_4$+).

4f) Methyl (4R)-7-[4-(4-(phenoxybutoxy)phenyl]-4-hydroxy-hept-5(Z)-eneoate

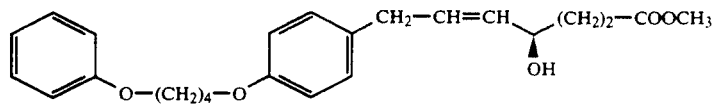

180 mg 10% Palladium on CaCO$_3$ suspended in 20 ml ethyl acetate and 4 ml freshly distilled quinoline are hydrogenated for 45 min. Acetylene-alcohol 6 (800 mg; 2.02 mmoles) dissolved in 20 ml ethyl acetate is added and hydrogenated under normal pressure. After 1 equivalent H2 is consumed, the suspension is filtered through Celite and washed thoroughly with 0.1M HCl and water, dried with Na$_2$SO$_4$ and evaporated. Flash-chromatography (SiO$_2$; 1% methanol in dichlormethane) yields 0.65 g (83%) pure (93% e.e.).

The following reaction steps to obtain the enantiomerically pure end product are carried out according to examples 2g,h, respectively 3i,j.

We claim:

1. A substituted alkenoic acid derivative of the formula

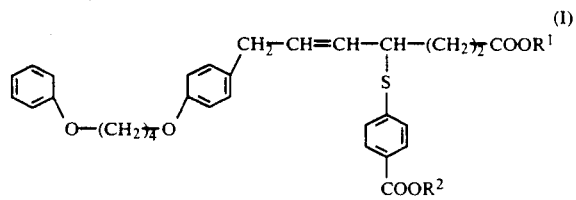

(I)

wherein
R$^1$, R$^2$ are identical or different and denote hydrogen, branched or straight-chain C$_1$-C$_6$-alkyl or benzyl, where appropriate in an isomeric form or a salt thereof.

2. A substituted alkenoic acid derivative of the formula according to claim 1, wherein
R$^1$, R$^2$ are identical or different and denote hydrogen or branched or straight-chain C$_1$-C$_6$-alkyl, where appropriate in an isomeric form or a salt thereof.

3. A substituted alkenoic acid derivative of the formula according to claim 1, wherein
R$^1$, R$^2$ are identical or different and denote hydrogen, methyl or ethyl, where appropriate in an isomeric form or a salt thereof.

4. A (+)- or (−)-enantiomer of the substituted alkenoic acid derivative according to claim 1.

5. 4-(4-Carboxyphenylthio)-7-[4-(4-phenoxybutoxy)-phenyl]hept-5(Z)enoic acid, a (+)- or (−)enantiomer thereof or a salt thereof.

6. 4(S)-(4-carboxyphenylthio)-7-[4-(4-phenoxybutoxy)phenyl)]hept-5(Z)-enoic acid or a salt thereof.

7. Composition for the treatment of allergic disorders, inflammation, cardiovascular disorders, cerebrovascular diseases and renal diseases comprising an amount effective therefor of a compound or salt thereof according to claim 1 and a pharmacological acceptable diluent.

8. Method of treating allergic disorders, inflammation, cardiovascular disorders, cerebrovascular diseases and renal diseases in a patient in need thereof which comprises administering to such patient an amount effective therefore of a compound or salt thereof according to claim 1.

9. An intermediate of the formula

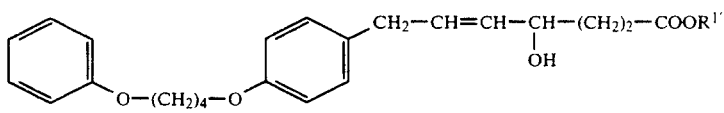

wherein R$^1$' denotes branched or straight-chain C$_1$-C$_6$-alkyl or benzyl where appropriate in an isomeric form.

* * * * *